(12) United States Patent
Ward et al.

(10) Patent No.: US 7,790,670 B2
(45) Date of Patent: *Sep. 7, 2010

(54) COMPOSITIONS AND METHODS FOR TREATMENT OF BODY WEIGHT CONDITIONS

(75) Inventors: Loren Spencer Ward, Twin Falls, ID (US); Eric Douglas Bastian, Twin Falls, ID (US); Starla Joyce Paulsen, Twin Falls, ID (US)

(73) Assignee: Glanbia Nutritionals (Ireland) Ltd., Kilkenny (IE)

( * ) Notice: Subject to any disclaimer, the term of this patent is extended or adjusted under 35 U.S.C. 154(b) by 311 days.

This patent is subject to a terminal disclaimer.

(21) Appl. No.: 10/969,468

(22) Filed: Oct. 20, 2004

(65) Prior Publication Data

US 2005/0106218 A1    May 19, 2005

Related U.S. Application Data

(63) Continuation-in-part of application No. 10/371,534, filed on Feb. 21, 2003.

(60) Provisional application No. 60/360,709, filed on Mar. 1, 2002.

(51) Int. Cl.
*A61K 38/17* (2006.01)
(52) U.S. Cl. .............................. 514/2; 424/682; 514/909
(58) Field of Classification Search ................. 424/755; 514/23, 2
See application file for complete search history.

(56) References Cited

U.S. PATENT DOCUMENTS

| | | | |
|---|---|---|---|
| 4,298,601 A | 11/1981 | Howard | |
| 4,833,128 A | 5/1989 | Solomon et al. | |
| 5,238,921 A * | 8/1993 | Maruyama et al. | 514/18 |
| 5,278,288 A | 1/1994 | Kawasaki et al. | |
| 5,280,107 A | 1/1994 | Kawasaki et al. | |
| 5,484,623 A | 1/1996 | McLean | |
| 5,683,725 A | 11/1997 | Malik et al. | |
| 5,739,106 A * | 4/1998 | Rink et al. | 514/12 |
| 5,855,949 A | 1/1999 | McLean | |
| 6,106,874 A | 8/2000 | Liebrecht et al. | |
| 6,136,349 A | 10/2000 | Karppanen et al. | |
| 6,207,638 B1 * | 3/2001 | Portman | 514/2 |

(Continued)

FOREIGN PATENT DOCUMENTS

GB    2348794    3/1999

(Continued)

OTHER PUBLICATIONS www.sciencedaily.com, "Calcium May Curb Weight Gain in Young Women", website, Apr. 1994, (adapted from a news release issued by Purdue University).

(Continued)

*Primary Examiner*—Neil Levy

(57) ABSTRACT

A nutritional supplement composition having therapeutically effective amounts of milk minerals including calcium, a protein source including κ-casein fragment 106-169, and enzyme-inhibiting peptides is provided for the treatment of body weight conditions. The nutritional supplement composition is administered in amounts effective for limiting weight gain and/or enhancing weight loss, as well as promoting overall good health, in the treatment of body weight conditions, including overweight and obesity.

4 Claims, 2 Drawing Sheets

U.S. PATENT DOCUMENTS

| | | | |
|---|---|---|---|
| 6,306,819 B1 | 10/2001 | Rupnick et al. | |
| 6,340,669 B1 | 1/2002 | Cestaro et al. | |
| 6,384,087 B1 | 5/2002 | Zemel et al. | |
| 6,384,088 B1 | 5/2002 | Hinz | |
| 6,998,259 B1 * | 2/2006 | Davis et al. | 435/219 |
| 2002/0025972 A1 | 2/2002 | Hinz | |
| 2002/0132014 A1 | 9/2002 | Zemel et al. | |
| 2002/0192264 A1 | 12/2002 | Zemel et al. | |
| 2004/0197382 A1 | 10/2004 | Zemel | |
| 2004/0197383 A1 | 10/2004 | Zemel | |
| 2004/0197385 A1 | 10/2004 | Zemel | |
| 2004/0197423 A1 | 10/2004 | Zemel | |
| 2004/0197424 A1 | 10/2004 | Zemel | |
| 2004/0197425 A1 | 10/2004 | Zemel | |

FOREIGN PATENT DOCUMENTS

| | | |
|---|---|---|
| JP | 04-158744 | 6/1992 |
| JP | 07-147935 | 6/1995 |
| JP | 09-173019 | 7/1997 |
| JP | 10-066513 | 3/1998 |
| WO | WO 99/11254 | 3/1999 |
| WO | WO 99/26971 | 6/1999 |

OTHER PUBLICATIONS

Susan Gaidos, "Calcium May Curb Weight Gain in Young Women", purduenews.purdue.edu, website, Jun. 1999.

Michael B. Zemel, "Nutritional and Endocrine Modulation of Intracellular Calcium: Implications in Obesity, Insulin Resistance and Hypertension", journal "Molecular and Cellular Biochemistry: An International Journal for Chemical Biology in Health and Disease", 1998, vol. 188, pp. 129-136, Kluwer Academic Publishers, Netherlands.

Robert C. Klesges, PhD, et al., "Predictors of Milk Consumption in a Population of 17-to-35-Year-Ol Military Personnel", Journal of the American Dietetic Association, , Jul. 1999, vol. 99, No. 7, pp. 821-838, publisher—Debra McBride.

Carolyn D. Summerbell,et al., "Randomised Controlled Trial of Novel, Simple, and Well Supervised Weight Reducing Diets in Outpatients", British Medical Journal, Nov. 28, 1998, vol. 317, pp. 1487-1489.

Lewis Landsberg, M.D., "Weight Reduction and Obesity", Clin. And Exper. Hypertension, 1999, vol. 21(5&6), pp. 763-768.

Yi-Chin Lin, MS, PhD, et al., "Dairy Calcium is Related to Changes in Body Composition During a Two-Year Exercise Intervention in Young Women", Journal of the American College of Nutrition, 2000, vol. 19, No. 6, pp. 754-760, published by the American College of Nutrition.

Judith Cook, et al., "The Contribution Made by School Milk to the Nutrition of Primary Schoolchildren", British Medical Journal, 1975, vol. 34, pp. 91-103, London.

Hang Shi, et al., "Role of Intracellular Calcium in Human Adipocyte Differentiation", Physiol Genomics, vol. 3, pp. 75-82, 2000 (article published online before print).

Bingzhong Xue, et al., "The *agouti* gene product inhibits lipolysis in human adipocytes via a $Ca^{2+}$—dependent mechanism", The FASEB Journal, vol. 12, pp. 1391-1396, Oct. 1998.

EJ Michaud, et al., "Obesity and the Adipocyte", Journal of Endocrinology, 1997, vol. 155, pp. 207-209, published in Great Britain.

Michael B. Zemel, et al., "Agouti Regulation of Intracellular Calcium: Role in the Insulin Resistance of Viable Yellow Mice", Proc. Natl. Acad. Science, vol. 92, pp. 4733-4737, May 1995.

Catherine B. Chan, et al., "Overexpression of Uncoupling Protein 2 Inhibits Glucose-Stimulated Insulin Secretion From Rat Islets", Diabetes, vol. 48, pp. 1-5, Jul. 1999.

J.R. Talbot, et al., "Calcium Bioavailability and Parathyroid Hormone Acute Changes After Oral Intake of Dairy and Nondairy Products in Healthy Volunteers", Osteoporosis International, vol. 10, pp. 137-142, 1999.

Scott Ackley, et al, "Dairy Products, Calcium, and Blood Pressure", The American Journal of Clinical Nutrition, vol. 38, pp. 457-461, Sep. 1983.

Merja UM Karkkainen, et al., "Postprandial Parathyroid Hormone Response to Four Calcium-Rich Foodstuffs", American Journal of Clinical Nutrition, vol. 65, pp. 1726-1730, 1997.

T. Vaskonen, et al., "Diet Enrichment with Calcium and Magnesium Enhances the Cholesterol-lowering Effect of Plant Sterols in Obese Zucker Rats", Nutr. Metab. Cardiovosc. Dis., vol. 11, pp. 158-167, 2001.

Michael B. Zemel, et al., "Regulation of Adiposity by Dietary Calcium", The FASEB Journal, vol. 14, pp. 1132-1138, Jun. 2000.

Hang Shi, et al, "Effects of Dietary Calcium on Adipocyte Lipid Metabolism and Body Weight Regulation in Energy-Restricted aP2-agouti Transgenic Mice", The FASEB Journal, vol. 15, pp. 291-293, Feb. 2001.

Hang Shi, et al., "Effects of Dietary Calcium on Adipocyte Lipid Metabolism and Body Weight Regulation in Energy-Restricted aP2-agouti Transgenic Mice", The FASEB Journal, express article 10.1096/fj.00-0584fje. Published online Dec. 8, 2000.

Jung Han Kim, et al., "The Effects of Calcium Channel Blockade on Agouti-Induced Obesity", The FASEB Journal, vol. 10, pp. 1646-1652, Dec. 1996.

L. Nordfors, et al., "Reduced Gene Expression of UCP2 but not UCP3 in Skeletal Muscle of Human Obese Subjects", Diabetologia, vol. 41, pp. 935-939, 1998.

J.H. Kim, et al., "Agouti Regulation of Intracellular Calcium: Role of Melanocortin Receptors", The American Physiological Society, vol. 35, pp. E379-E384, 1997.

H. Oberkofler, et al., "Uncoupling Protein-2 Gene: Reduced mRNA Expression in Intraperitoneal Adipose Tissue of Obese Humans", Diabetologia, vol. 41, pp. 940-946, 1998.

Hang Shi, et al., "Role of the Sulfonylurea Receptor in Regulating Human Adipocyte Metabolism", The FASEB Journal vol. 13, pp. 1833-1838, Oct. 1999.

J.A. Metz, et al., "Modification of Total Body Fat in Spontaneously Hypertensive Rats and Wistar-Kyoto Rats by Dietary Calcium and Sodium", The American Journal of Hypertension, vol. 1, pp. 58-60, 1988.

National Dairy Council, "Study Heralds the Power of Lowfat Dairy Foods in Helping Control Body Fat and Helping Reduce the Risk of Obesity", press release, Nov. 17, 1999.

Peter G. Kopelman, "Obesity as a Medical Problem", International Weekly Journal of Science, Apr. 6, 2000, vol. 404, pp. 631-677.

Brynn H. Jones, et al., "Angiotensin II Increases Lipogenesis in 3T3-L1 and Human Adipose Cell[108]", The Endocrine Society, vol. 138, #4, pp. 1512-1519.

Jones BH, et al., "Angiotensinogen Gene Expression in Adipose Tissue: Analysis of Obese Models and Hormonal and Nutritional Control", American Journal of Physiology, Jul. 1997, pp. 236-242.

BR Carruth, et al., "The Role of Dietary Calcium and Other Nutrients in Moderating Body Fat in Preschool Children", International Journal of Obesity, 2001, vol. 25, pp. 559-566.

Linda K. Massey, "Dairy Food Consumption, Blood Pressure and Stroke", American Society for Nutritional Sciences, 2001, pp. 1875-1878.

Robert P. Heaney, "Calcium Needs of the Elderly to Reduce Fracture Risk", Journal of the American College of Nutrition, vol. 20, No. 2, 2001, pp. 192S-197S.

Sylvie Beucher, et al, "Effects of Gastric Digestive Products from Casein on CCK Release by Intestinal Cells in Rat", Nutritional Biochem, vol. 5, 1994, pp. 578-584.

Ernest P. Brody, "Biological Activities of Bovine Glycomacropeptide", British Journal of Nutrition, 2000, vol. 84, pp. S39-S46.

JC Blum, Proceedings of the Symposium on Animal and Human Nutrition, Jan. 1994, pp. 612-613.

E.YA. Stan, et al., "Effect of X-Casein Glycomacropeptide on Gastrointestinal Motility in Dogs", Laboratory of Protein Metabolism, Institute of Nutrition, Academy of Medical Sciences of the USSR, Moscow.

Nathalie Ledoux-Rolf Pedersen, et al. "Caseinomacropeptide Specifically Stimulates Exocrine Pancreatic Secretion in the Anesthetized Rat", Peptides, vol. 21, 2000, pp. 1527-1535.

K. Michael Davies, et al., "Calcium Intake and Body Weight", The Journal of Clinical Endocrinology and Metabolism, Dec. 2000, vol. 85, pp. 4635-4638.

TruCal, 2001, Glanbia Ingredients, Ltd.

TruCal FP, 2001 Glanbia Ingredients, Ltd.

TruCal, Sep. 2001, Glanbia Ingredients, Ltd.

P. Guilloteau, et al., "Effect of Caseinomacropeptide on Gastric Secretion and Plasma Gut Regulatory Peptides in Preruminant Calves", Proceedings of the Symposium on Animal and Human Nutrition, Jan. 1994, p. 612.

S. Beucher, et al., "Effect of Caseinomacropeptide (CMP) on Cholecystokinin (CCK) Release I Rat", Proceedings of the Symposium on Animal and Human Nutrition, Jan. 1994, p. 613.

Kim S., et al., "Angiotensin II-Responsive Element is the Insulin-Responsive Element in the Adipocyte Fatty Acid Synthase Gene . . . ", Journal of Biochemistry, Aug. 1, 2001, vol. 357.

Kim, S., et al., "Secretory, Endocrine and Autocrine/Paracrine Function of the Adipocyte", Journal of Nutrition, Dec. 2000, vol. 130.

U.S. Appl. No. 11/091,924, filed Mar. 29, 2005.

M.B. Zemel; "Role of Calcium and Dairy Products in Energy Partitioning and Weight Management"; Am J Clin Nutr, 2004; 79 (suppl), pp. 907S-912S.

Y. Hata, M. Yamamoto, M. Ohni, K. Nakajima, Y. Nakamura and T. Taken, "A Placebo-Controlled Study of the Effect of Sour Milk on Blood Pressure in Hypertensive Subjects", Am J Clin Nutr, 1996;64, pp. 767-771.

L. Seppo, T. Jauhiainen, T. Poussa and R. Korpela, "A Fermented Milk High in Bioactive Peptides Has a Blood Pressure-Lowering Effect in Hypertensive Subjects", Am J Nutr 2003;77 pp. 326-330.

"Information About the Evolus® Fermented Milk", Valio, Ltd., R&D, 2002.

T. Jauhiainen, "Evolus, Bioactive Peptides in Evolus Lower the Blood Pressure of Hypertensive Subjects", Valio Foods & Functionals Jan. 2003 pp. 16-17.

Beevers, D.G. et al., Enalapril in Essential Hypertension: A Comparative Study With Propanolol, Br. J. Clin. Pharmacol. (1984) 18: 51-56.

Jayasooriya, A.P. et al., Mice Lacking Angiotensin-Converting Enzyme Have Increased Energy Expenditure, with Reduced Fat Mass and Improved Glucose Clearance, PNAS (May 6, 2008) 105(18): 6531-6536.

* cited by examiner ately effective nutritional supplement composition. More particularly, the nutritional composition, which includes bioavailable calcium and protein components, is effective for enhancing weight loss and/or limiting weight gain.

COMPOSITIONS AND METHODS FOR TREATMENT OF BODY WEIGHT CONDITIONS

CROSS REFERENCE TO RELATED APPLICATIONS

This application is a continuation-in-part of U.S. patent application Ser. No. 10/371,534 filed on Feb. 21, 2003, which claims the benefit of U.S. Provisional Application No. 60/360,709, filed on Mar. 1, 2002, the disclosures of which are both incorporated herein by reference.

BACKGROUND OF THE INVENTION

The present invention is directed to compositions and methods for treatment of body weight conditions by administering a therapeutically effective nutritional supplement composition. More particularly, the nutritional composition, which includes bioavailable calcium and protein components, is effective for enhancing weight loss and/or limiting weight gain.

Obesity is a significant worldwide health concern that affects both young and old. In the United States, it is estimated that more than 50% of men and women are overweight. The degree to which a person may be overweight can be evaluated based on the person's "body mass index" or "BMI", which is calculated as follows:

$$BMI=\text{Weight in kilograms (kg)}/[\text{Height in meters (m)}]^2.$$

In 2000, almost 20% of the population fell into the obese category as defined by a BMI of greater than or equal to 30. Problems associated with obesity include cardiovascular disease, diabetes mellitus, certain types of cancer, osteoarthritis and sleeping disorders. Obesity and related disorders account for almost 10% of US health care expenditures.

Over 90% of body energy is stored in adipose (fat) tissue. Adipose tissue has a number of important functions, the most obvious of which is to "buffer" the daily influx of dietary fat entering the blood circulation and release fatty acids as a source of metabolic fuel when needed. Other functions include the production and release of adipsin (essential for blood clotting), angiotensinogen (involved in blood pressure control), and leptin (a hormone involved in energy control). An accumulation of adipose tissue leads to overweight and obesity.

Diet is known to have effects on weight control. Excesses in diet, such as high caloric intake and consumption of high fat foods, can result in undesired weight gain and poor health. Similarly, a diet lacking one or more nutrients also can have a negative impact on weight control and health. For example, literature suggests that that a diet deficient in calcium can contribute to the occurrence obesity. Shi et al., "Effects of dietary calcium on adipocyte lipid metabolism and body weight regulation in energy-restricted aP2-agouti transgenic mice" *FASEB J.* 15(2), 291-93 (2001); Zemel et al., "Regulation of adiposity by dietary calcium," *FASB J.* 14(9) 1132-38 (2000).

Mechanisms in the human body also are known to impact weight gain. For example, when food is consumed, the body releases a peptide, cholecystokinin (CCK), which acts to signal satiety as a result of promoting secretion of enzymes and other bodily fluids and other physical reaction within the gastric system. It has been shown that CCK release results in appetite reduction so that the person will stop eating. Proteins such as κ-casein fragment 106-169, also referred to as glycomacropeptide (GMP), are known to stimulate the release of CCK.

Various weight control compositions and methods for use by overweight and obese adults are known. Typically, however, the methods focus on a particular weight control mechanism in order to control weight gain or promote weight loss, with little or no regard for providing a balanced diet. For example, U.S. Pat. No. 6,384,087 to Zemel discloses methods and materials for treating or avoiding obesity in humans and other animals. The patent discloses that the obesity-control benefits can be achieved by providing a diet high in calcium. Additionally, the patent teaches that individuals are maintained on a restricted caloric diet. The weight control mechanism of this patent is directed to providing increased levels of one specific nutrient, calcium, while optionally limiting caloric intake, without promoting a balanced diet. As another example, U.S. Pat. No. 6,207,638 to Portman discloses a nutritional intervention composition for enhancing and extending satiety by stimulating the release of CCK. The composition includes a protein, a glycomacropeptide, long chain fatty acids, calcium (in the form of calcium carbonate or calcium lactate) and a combination of soluble and insoluble fibers. The patent teaches that the composition can be taken orally to permit a person to be satiated with a lower calorie intake. The weight management mechanism of this composition is directed to limiting caloric intake, without addressing overall nutritional requirements.

There remains a need for methods of improving human diets in order to maintain an ideal weight, reduce weight gain and/or enhance weight loss while promoting a nutritionally balanced diet. There also remains a need for dietary compositions to provide essential nutrients associated with a healthy diet to reduce incidence of overweight and obesity and maintain overall health.

SUMMARY OF THE INVENTION

The present invention is directed to compositions for the management of body weight and treatment of body weight conditions, such as overweight or obesity. According to one aspect of the invention, a weight control composition is provided that includes one or more of a milk mineral blend in an amount effective for decreasing adiposity, a protein compound in an amount effective for enhancing satiety after consumption of food, and enzyme-inhibiting peptides in an amount effective for controlling fat metabolism. The milk mineral blend includes calcium, and the protein compound includes κ-casein fragment 106-169. According to another aspect of the invention, a nutritional supplement for maintaining and/or reducing weight is provided. The supplement can include a milk mineral composition having calcium in an amount effective for decreasing adiposity. The supplement also can include a protein composition having κ-casein fragment 106-169 in an amount effective for enhancing satiety to limit or curtail consumption of food. The supplement also can include enzyme-inhibiting peptides, such as angiotensin converting enzyme-inhibiting peptides, in an amount effective for enhancing weight loss in treating an overweight condition or obesity.

According to yet another aspect of the invention, methods of maintaining a desired weight and treating an overweight condition or obesity include administering to an individual in need of such treatment a nutritional composition limiting weight gain and/or enhancing weight loss, as well as promoting overall good health. The composition can include therapeutically effective amounts of a milk mineral component, a protein component and/or an enzyme-inhibiting peptide component. The composition can be taken directly by an individual or administered via a food product fortified with the composition. The amount of nutritional supplement composition when administered via a food product can be suitably selected, for example, such that a daily serving or a predetermined number of servings of the food product delivers an amount of the composition effective for maintaining a desired weight or treating an overweight condition or obesity. The composition can be administered just prior to or after consumption of food, as part of a meal or as a snack between meals.

The nutritional supplement composition, generally in the form of a powder of appropriate particle size, can be incorporated into a wide variety of types of food products. By way of example, the nutritional composition can be added to acidic juice beverages (e.g., orange juice, apple juice, grape juice, grapefruit juice, cranberry juice, or blended juices), acidic beverages (e.g., sport beverages, Gatorade®), neutral pH beverages (e.g., milk UHT dairy, RTD nutritional, soy milk, or shakes and other blended beverages such as milkshakes, smoothies, frappes), nutritional supplement foodstuffs (e.g., high-energy protein bars), confectionery products (e.g., high calcium chews, chewing gum, chocolate, or cookies), dairy products (e.g., yogurt, ice cream, milk, cheese, processed cheese, or butter), and farinaceous products (e.g., bread, muffins, biscuits, cereal or rolls). Alternatively, the nutritional supplement composition can be administered directly, such as in the form of tablets or capsules and optionally combined with other minerals and/or vitamins.

DETAILED DESCRIPTION OF THE INVENTION

Figure 1:
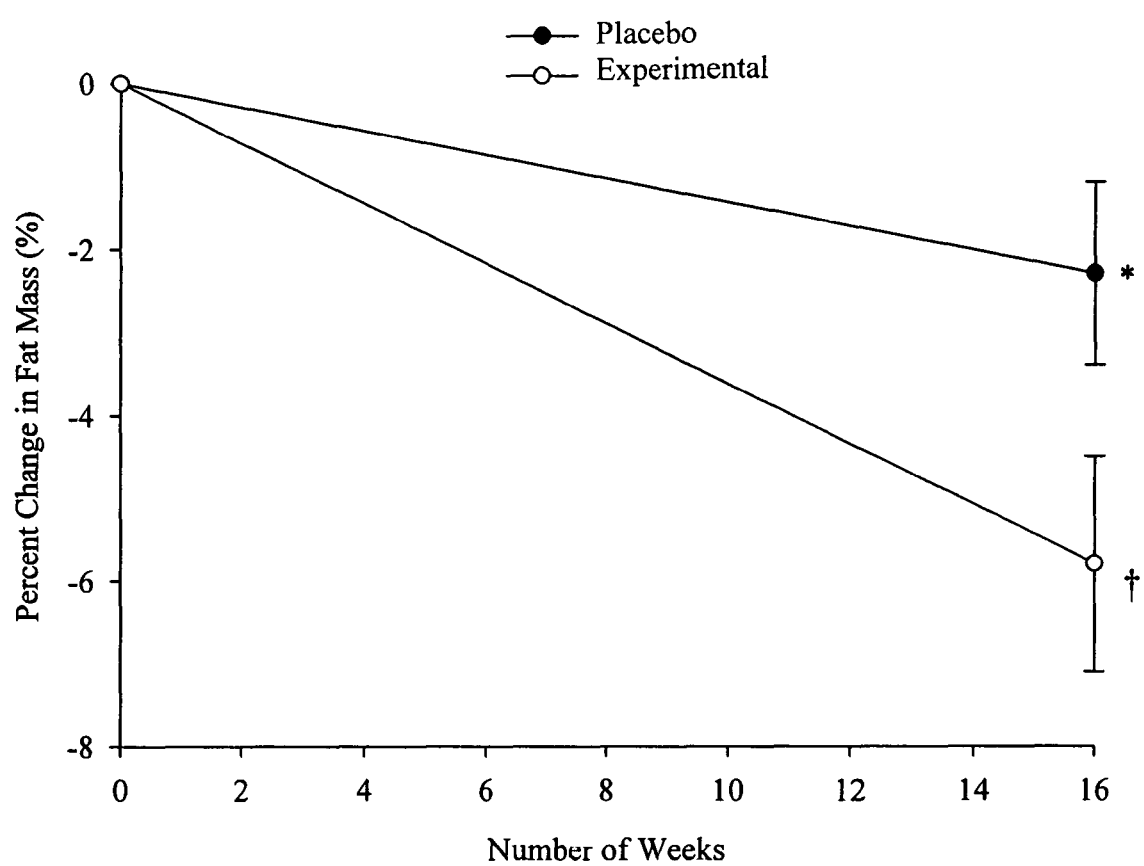
FIG. 1 is a graph illustrating the change in body fat mass with a composition in accordance with the present invention as compared with a placebo.

The present invention is directed to compositions and methods for maintaining a predetermined body weight range and treating an overweight condition or obesity by enhancing weight loss and/or limiting weight gain and promoting good health. Overweight and obesity has been associated to some degree with inadequate intake of dairy products, and more particularly the minerals present in dairy products. It has been discovered that an overweight condition and obesity can be effectively treated by administering nutritional supplement compositions, either directly or via food products fortified with the compositions, in accordance with the practice of the present invention. The nutritional supplement compositions contain therapeutically effective amounts of milk mineral, protein and enzyme-inhibiting peptides and are administered prior to or during a meal. The nutritional supplement compositions also can be administered to an individual seeking to maintain a desired body weight.

Treatment can be enhanced by use of additional ingredients in the composition to address other mechanisms for weight control. The compositions can include κ-casein fragment 106-169 (or a source of such peptides) to limit caloric intake by providing a sense of satiety, which will lead to termination of eating. Additionally, enzyme-inhibiting peptides may be included to assist with regulation of adiposity by controlling fat metabolism.

The terms "treat," "treating," "treatment," and similar terms as used herein refer to the administration of the nutritional supplement compositions to individuals, particularly humans, who are overweight or obese, for alleviating, suppressing, inhibiting, or otherwise reducing the extent to which the individual is overweight or obese or any symptom associated therewith. The terms "treat," "treating," "treatment," and similar terms also are used herein to refer to the prophylactic administration of the nutritional supplement compositions to individuals who may be at risk of, or otherwise wish to avoid, becoming overweight or obese.

The nutritional supplement composition includes a source of calcium. Possible sources of calcium include dairy sources, such as milk, and non-dairy sources, including but not limited to calcium carbonate, calcium lactate, calcium citrate, calcium phosphate, calcium chloride, and calcium hydroxide. In preferred embodiments, milk mineral provides the available calcium. The term "milk mineral," as used herein, refers to a mineral complex obtained from whey or milk. The mineral complex contains a balanced form of calcium, copper, magnesium, phosphorus, potassium, selenium and zinc. The term "milk mineral," as used herein, refers to a mineral complex obtained from whey or milk and having a balanced form of minerals selected from the group consisting of calcium, magnesium, potassium, phosphorus, copper, selenium, and zinc and the like. Milk mineral has a relatively neutral taste, in contrast to the chalky taste of calcium carbonate. Whey fractions that are high in calcium have been demonstrated to exhibit higher calcium bioavailability than are exhibited by calcium carbonate and calcium lactate. Ranhotra et al., "Bioavailability of Calcium in a High Calcium Whey Fraction," *Nutrition Research*, Vol. 17 Nos. 11-12, pp. 1663-1670 (1997). For optimal absorption, calcium and phosphorous preferably are present in a calcium-to-phosphorous ratio of about 1:1 to 2:1, e.g., a ratio similar to that found in both milk and in bone. The milk mineral also typically contains quantities of lactose and bioactive proteins. Milk mineral is also commonly referred to as "milk calcium."

Milk mineral provides various benefits as compared to supplements having other forms of calcium. Calcium supplements and calcium-fortified foods contain calcium in such forms as calcium carbonate, calcium lactate, calcium citrate, calcium chloride, and calcium hydroxide. These forms of calcium, however, can yield undesirable flavors and/or can strip desirable aroma and flavor compounds from food products. Use of milk minerals can avoid these problems. More significantly, the milk mineral complex delivers not only calcium but a balanced and pure form of the other milk minerals, including copper, magnesium, phosphorus, potassium, selenium and zinc, that are present only in milk and dairy products and that are important to a healthy diet. As a result, the milk mineral complex provides a balanced form of minerals, including calcium that is a preferred form of calcium and other minerals from a nutritional standpoint.

Suitable methods of obtaining milk mineral by extraction from whey or milk are known to persons skilled in the art. One suitable extraction method is described in U.S. Pat. No. 5,639, 501, the disclosure of which hereby is incorporated by reference in its entirety. Additionally, commercially available milk mineral products include TRUCAL® products, which are commercially available from Glanbia Nutritionals, Inc. of Monroe, Wis. A typical composition of milk mineral is illustrated in Table 1 below.

TABLE 1

Typical Composition for Milk Mineral Powder

| Component | Relative Amount (% by weight) |
|---|---|
| Total Minerals | 50-90% |
| Inorganic Mineral (Ash) | 45-85% |
| Organic Mineral (Citrate) | 1-10% |
| Calcium | 15-35% |
| Magnesium | 0-10% |
| Phosphorous | 7-15% |
| Potassium | 0-5% |
| Zinc | 0-1% |
| Lactose | 0-15% |
| Protein | 1-15% |
| Free Moisture | 2-5% |
| Fat | 0-5% |

One important attribute of milk mineral is the calcium-to-magnesium ratio. Predetermined calcium-to-magnesium ratios are desired to limit or avoid leaching of other important minerals, which in turn may lead to bone brittleness and can even increase the risk of osteoporosis. Without wishing to be bound by any theories, high dietary Ca:Mg ratios interfere with magnesium absorption because calcium and magnesium share common intestinal absorption pathways. When calcium levels are high with respect to magnesium levels, for example, above about 30:1, calcium competes with magnesium for the absorption pathways, resulting in hypomagnesaemia (low magnesium in the blood).

The natural milk minerals, especially calcium, copper, magnesium, phosphorus, potassium, selenium and zinc, are of great importance in nutrition. Calcium, for example, is essential to many body functions, such as muscle function regulation, blood clotting, hormone regulation, nerve function, and enzyme activation. Calcium in milk mineral has a high bioavailability, which is enhanced by vitamin D, lactose, gastrointestinal acidity, and certain fibers. Also, the balanced form of calcium, copper, magnesium, phosphorus, potassium, selenium and zinc, and vitamin D in milk mineral helps to minimize calcium depletion through urinary loss.

The balance of minerals and bioactive proteins in the milk mineral renders food products fortified with the compositions of the present invention effective for healthy weight maintenance and in the treatment of the conditions of overweight and obesity. While not wanting to be bound by any theory, the following provides a discussion of the various mechanisms by which body weight conditions can be treated using the compositions of the present invention.

The milk minerals of the present compositions provide high calcium bioavailability effective for managing body weight and treating conditions including overweight and obesity. A common metabolic defect in cellular calcium ion handling is thought to contribute to the occurrence of weight gain and obesity. Low calcium intake increases intracellular calcium concentration in the adipocyte (fat cell) thereby switching its metabolism from lipolysis (fat breakdown) to lipogenesis (fat synthesis) and fat accumulation. By increasing the amount of calcium intake, intracellular calcium concentration is reduced, which leads to increased lipolysis and decreased lipogenesis. Thus, it is desired to provide a daily intake of an amount of calcium effective for weight maintenance and/or loss through reduction of fat tissue mass.

In another aspect of the present invention, the nutritional supplement composition includes a protein source such as whey proteins or other suitable food protein. Whey proteins occur in milk as soluble, globular proteins. Generally, they are an important source of protein needed for overall good health and nutrition. The primary proteins and peptide constituents derived from whey proteins include α-lactalbumin and β-lactoglobulin, κ-casein fragment 106-109, lactoferrin, bovine serum albumin, lactoperoxidase, and immunoglobulins. The composition also may include high branched chain amino acids, such as leucine.

An important peptide constituent is κ-casein fragment 106-109. These peptides function as an appetite suppressant by stimulating the release of the gastrointestinal hormone CCK. CCK is effective for short-term control of eating behavior because it generates responses in the body that are associated with satiety, thereby resulting in termination of the meal. Thus, by administering an effective amount of κ-casein fragment 106-169 prior to, during, or even shortly after a meal, the amount of food eaten during a meal can be limited while providing a sense of satiety. Additionally, administering κ-casein fragment 106-169 between meals when a person may feel hungry may also provide a sense of satiety, thereby avoiding undesired snacking between meals.

Sources of κ-casein fragment 106-169 include PROVON® 190 and PROVON® 290, which are commercially available from Glanbia Nutritionals, Inc. of Monroe, Wis. Suitable methods for producing κ-casein fragment 106-169 are known to those of skill in the art and are, for example, described in U.S. Pat. Nos. 5,278,288 and 5,280,107, incorporated herein by reference in their entirety, which describe processes for producing κ-casein fragment 106-169 from milk raw materials such as cheese whey and whey protein concentrates.

In another aspect of the present invention, the composition includes enzyme-inhibiting peptides. Sources of such peptides include casein, whey proteins, soy proteins, wheat proteins, rice proteins, pea proteins, fish proteins or any other suitable commercially available food protein which can be processed according to any methods known to those of skill in the art to provide the peptides. One example of such peptides are those that inhibit angiotensin converting enzyme (ACE). Angiotensin II is a hormone that is synthesized and secreted by adipose cells. Angiotensin II may be involved in control of adiposity through regulation of lipid synthesis and storage of adipocytes. Some dairy peptides are associated with the inhibition of angiotensin converting enzyme (ACE). Thus, by administering a therapeutically effective amount of ACE-inhibiting peptides, weight loss can be enhanced. Another type of enzyme-inhibiting peptides are those that will inhibit the enzymatic breakdown of CCK. One or more enzyme-inhibiting peptides can be included in the composition.

To obtain compositions of the present invention, the components selected for the compositions can be processed as desired prior to preparation of the nutritional supplement compositions. Milk mineral extract typically is purified, spray dried, and ground into a powder having an appropriate particle size to permit mixing with a liquid or solid food product if desired. The milk mineral extract has calcium and other minerals as shown in Table 1. Similarly, the protein component typically is purified, dried, and ground into a powder. The protein component has κ-casein fragment 106-169 and, if desired, amino acids and other nutrients essential for overall good health and nutrition. ACE-inhibiting peptides also can be provided in the nutritional supplement composition. The desired components, which are selected from milk mineral extract, protein component and ACE-inhibiting peptides and combinations thereof, are blended to provide the nutritional supplement compositions of the present invention. The composition optionally can include other ingredients, such as minerals, vitamins, flavorings and colorants, in accordance with techniques well known to persons skilled in the art.

Suitable particle sizes for the composition will depend on such factors as the physical properties (e.g., liquid or solid, specific gravity, pH, viscosity, etc.) of the food product into which the powder is mixed. The mean particle size most often ranges from about 0.1 microns to about 300 microns, more usually from about 1 micron to about 100 microns. For neutral pH beverages, such as milk, a more finely ground powder preferably is employed so that a suspension of the powder can be easily formed. Because the solubility of the powder increases as pH decreases, less finely ground powders typically can be used, for example, in acidic juice beverages and in acidic beverages, in which the powder solubilizes.

The nutritional supplement composition in powder form can be used as an additive for a wide variety of types of food products, including acidic juice beverages (e.g., orange juice, apple juice, grape juice, grapefruit juice, cranberry juice, or blended juices), acidic beverages (e.g., sport beverages, Gatorade®), neutral pH beverages (e.g., milk UHT dairy, RTD nutritional, soy milk, or shakes and other blended beverages such as milkshakes, smoothies, frappes), nutritional supplement foodstuffs (e.g., high-energy protein bars), confectionery products (e.g., high calcium chews, chewing gum, chocolate, or cookies), dairy products (e.g., yogurt, ice cream, milk, cheese, processed cheese, or butter), and farinaceous products (e.g., bread, muffins, biscuits, cereal or rolls). The relative amount by weight of the nutritional supplement compositions combined with a food product depends on such factors as the density and the serving size of the food product. Typically, the amount of nutritional supplement compositions ranges from 0.1 to about 10 percent by weight, based on the total weight of the food product.

Alternatively, the nutritional supplement composition can be prepared in a form to be directly administered to an individual. By way of example, the composition can be prepared in the form of tablets, chewable tablets, capsules, and liquid syrup.

The formulation of the composition and, if administered via a food product, the amount of the composition blended into the food product, are selected to provide desired amounts of the particular components so as to be effective for controlling weight gain and/or weight loss. By way of example, a typical nutritional supplement composition may be administered to provide between at least about 0.5 and about 6 grams or more of calcium, between at least about 0 and about 10 grams or more of κ-casein fragment 106-169, and between at least about 0 to about 20 grams or more of ACE-inhibiting peptides per serving of the composition. The amount of composition administered can be adjusted as desired to account for differences in physical characteristics and nutritional requirements of the individuals to whom the composition is administered.

In accordance with the methods of the present invention, body weight conditions, including overweight and obesity, are effectively managed and treated. That is, an individual of healthy condition and having a generally ideal weight can manage his weight and maintain a desired weight range. An individual who has a weight in excess of a desired range, and may be considered overweight or obese, can be effectively treated by limiting weight gain and/or promoting weight loss. A therapeutically effective amount of the nutritional supplement composition is administered to an individual to provide these benefits.

EXAMPLES

The following examples further illustrate preferred embodiments of the present invention but are not be construed as in any way limiting the scope of the present invention as set forth in the appended claims.

Example 1

This example illustrates preparation of a beverage fortified with a nutritional supplement composition. The components were mixed to yield a product having the composition set forth in Table 2.

TABLE 2

| Ingredient | Amount (weight %) | Weight (grams) |
| --- | --- | --- |
| Water | 70.03 | 350.17 |
| PROVON ® 190* | 10.71 | 53.55 |
| Crystalline fructose | 7.00 | 35.00 |
| TRUCAL ® FP D7* | 1.48 | 7.38 |
| Carrageenan | 0.08 | 0.40 |
| Maltodextrin | 10.00 | 50.00 |
| Flavor | 0.70 | 3.50 |
| Color | 0.001 | 0.005 |

*Available from Glanbia Nutritionals Inc., of Monroe, Wisconsin

The liquid ingredients and carrageenan were mixed on high speed for about 5 minutes for hydration. The remaining dry ingredients were blended together and added slowly to the liquid mixture and mixed on low speed for between about 5 to about 10 minutes.

An 11-ounce serving of the fortified drink provides 1 gram of calcium, 30 grams protein, 6 grams of κ-casein fragment 106-169, and 1 gram of ACE-inhibiting peptide components.

Example 2

This example illustrates a formulation for a first dry beverage mix fortified with a nutritional supplement composition. The components were mixed to yield a product having the composition set forth in Table 3.

TABLE 3

| Ingredient | Amount (weight %) | Weight (grams) |
| --- | --- | --- |
| PROVON ® 190* | 45 | 18.5 |
| TRUCAL ®* | 10 | 4 |
| Protein Component/ACE-inhibiting peptide source | 10 | 4 |
| Fructose | 31 | 13 |
| Carrageenan | <1 | 0.3 |
| Dispersion Aids | <1 | 0.3 |
| Flavor | 3 | 1.4 |
| Color | <1 | <0.1 |

*Available from Glanbia Nutritionals Inc., of Monroe, Wisconsin

The dry mix is prepared to be ready for mixing with a sufficient volume of a desired liquid, such as water or skim milk, to provide a beverage.

A single serving (41.5 grams) of the dry mix delivers about 127 calories, about 20 grams of protein, about 1 gram of calcium, about 4 grams of κ-casein fragment 106-169, and about 2 grams of ACE-inhibiting peptide components.

Example 3

This example illustrates a formulation for a second dry beverage mix fortified with a nutritional supplement composition. The components were mixed to yield a product having the composition set forth in Table 4.

TABLE 4

| Ingredient | Amount (weight %) | Weight (grams) |
|---|---|---|
| PROVON ® 190* | 45 | 18.5 |
| TRUCAL ®* | 10 | 4 |
| Protein Component/ACE-inhibiting peptide source | 10 | 4 |
| Fructose | 31 | 13 |
| Carrageenan | <1 | 0.3 |
| Dispersion Aids | <1 | 0.3 |
| Flavor | 4 | 1.8 |
| Color | <1 | <0.1 |

*Available from Glanbia Nutritionals, Inc., of Monroe, Wisconsin.

The dry mix is prepared to be ready for mixing with a sufficient volume of a desired liquid, such as water or skim milk, to provide a beverage.

A single serving (41.5 grams) of the dry mix delivers about 125 calories, about 20 grams of protein, about 1 gram of calcium, about 4 grams of κ-casein fragment 106-169, and about 4 grams of ACE-inhibiting peptide components.

Example 4

This example illustrates a formulation for a third dry beverage mix fortified with a nutritional supplement composition. The components were mixed to yield a product having the composition set forth in Table 5.

TABLE 5

| Ingredient | Amount (weight %) | Weight (grams) |
|---|---|---|
| PROLIBRA ®* | 54 | 27 |
| Fructose | 27 | 13.3 |
| Maltodextrin | 5 | 2.6 |
| Carrageenan | 1 | 0.5 |
| Flavor | 13 | 6.6 |

*Available from Glanbia Nutritionals, Inc., of Monroe, Wisconsin

The dry mix is prepared to be ready for mixing with a sufficient volume of a desired liquid, such as water or skim milk, to provide a beverage. A single serving (50 grams) of the dry mix delivers about 162 calories, about 21 grams of protein, about 1 gram of calcium, about 4 grams of κ-casein fragment 106-169, and about 4 grams of ACE-inhibiting peptide components.

Example 5

This example describes a double-blind, randomized, placebo-controlled study that evaluated weight loss following the administration of an effective amount of a whey protein nutritional composition.

The study included overweight and obese adults who otherwise were in good health. The subject men and women had to be at least 18 years old, have a BMI of 27-42 kg/m$^2$, and be in good health. Subjects had to be willing to ingest more than 1.5 servings of dairy products (more than 500 mg calcium per day) during the course of the study, regardless of the source, and also had to be willing to follow a mildly hypocaloric diet to produce a 500-800 kcal/day energy deficit. Subjects were asked to maintain their usual levels of activity throughout the trial.

During the course of the study, subjects were not allowed to use: meal replacement products; dietary supplements (multi-vitamins containing less than 200 mg calcium were acceptable); systemic corticosteroids, androgens, phenytoin, or pseudo-ephedrine; lipid-lowering therapy drugs (unless dose stable for 2 months prior to enrollment); drugs for regulating hemostasis (other than stable dose aspirin); thyroid hormones (except stable-dose replacement therapy for more than 2 months prior to enrollment); or psychiatric medications.

Experimental Compositions

The participants were randomly assigned to either an experimental group or a control group. Subjects in the experimental group received a dietary supplement having 42 grams of powdered mix containing 26.5 grams of PROLIBRA®, commercially available from Glanbia Nutritionals, Inc., of Monroe, Wis. Subjects in the control group received a carbohydrate placebo having 42 grams of powdered mix as a matching control. The compositions of the experimental and control compositions are set forth in Table 6. The study products contained similar total calories, but contained no fat, fiber, or alcohol (see Table 6). Subjects were instructed to consume the study product once each day by mixing one packet with 8 ounces of cold water and drinking it prior to breakfast. All products were packaged in individual serving packets labeled with a blinding code.

TABLE 6

| Primary Energy Source | Control | Experimental |
|---|---|---|
| Energy (kcal) | 140 | 150 |
| Carbohydrate (g) | 35 | 14 |
| Protein (g) | <0.1 | 20 |
| Total Fat (g) | 0.2 | 0.9 |
| Dietary Fiber (g) | 0 | 0 |
| Cholesterol (mg) | 0 | 5 |
| Iron (mg) | <0.1 | 1.8 |
| Sodium (mg) | 2 | 140 |
| Calcium (mg) | 0 | 1100 |
| Potassium (mg) | 9 | 124 |
| Magnesium (mg) | 0 | 65 |

Study Design

Reductions in body fat, overall body weight, waist circumference, and deviations in serum chemistry and immune cell counts were measured at predetermined sample collections beginning at week 0 and continuing until completion of the study at week 16.

Clinic Visits

The study used a randomized, controlled design with two parallel treatment arms. The study included seven clinic visits: one screening visit at week −2, one at baseline visit at week 0, and five visits during treatment at weeks 2, 4, 8, 12, and 16. All clinic visits took place within ±4 days of the scheduled visit. All post-randomization visits (weeks 2, 4, 8, 12, and 16) occurred based on the date projected from the day of randomization (week 0). Subjects were to abstain from all foods and beverages (except water) for at least 12 hours prior to all clinic visits and abstain from consuming alcohol 24 hours prior to all clinic visits.

Weight and waist circumference were measured at each clinic visit. Three-day diet records were dispensed to subjects with instructions to record all food, beverage, medication, study product, and supplement intake for three consecutive days (two weekdays and one weekend day) prior to week 0 (visit 2) Diet records were collected, reviewed, and analyzed using the University of Minnesota Nutrition Data System for Research (NDS-R), version 4.05_33 (2002). Subjects also completed the Stanford 7-Day Physical Activity Recall questionnaire. Body composition analysis was performed with a dual energy x-ray absorptiometry (DEXA) scanner.

Subjects were randomly assigned to receive either the whey protein mixture or matching control during the 16-week trial. Subjects were instructed to follow a mildly hypocaloric diet to produce a 500-800 kcal/day energy deficit for the 16-week treatment period, with dietary counseling reinforced at each subsequent visit. Recommended energy intake was calculated as follows according to (Schofield 1985):

Recommended energy intake in kcal/day=(estimated basal metabolic rate×1.3)−600, where the estimated basal metabolic rate was calculated for specific sex and age groups as follows:

Males 18-30 years old=[(0.0630×weight in kg)+2.8957]×240 kcal/day

Males ≧31 years old=[(0.0484×weight in kg)+3.6534]×240 kcal/day

Females 18-30 years old=[(0.0621×weight in kg)+2.0357]×240 kcal/day

Females ≧31 years old=[(0.0342×weight in kg)+3.5377]×240 kcal/day

During the treatment period visits (weeks 2, 4, 8, 12, and 16), assessment of study product compliance, adverse events, and concomitant medication use were made. New 3-day dietary records were issued at these visits and completed records were collected and reviewed by the dietician. Also at week 16 (visit 7), body fat mass analysis was repeated with DEXA. The Stanford 7-Day Physical Activity Recall questionnaire was administered and the 3-day dietary record was collected, reviewed, and analyzed.

Statistical Analyses

Statistical analyses were conducted using the SAS version 8.02 statistical analysis package (SAS Institute, Cary, N.C.). Parametric and non-parametric analyses were used as required to assess responses within and between treatment groups for responses. All pair-wise tests for significance were performed at $\alpha=0.05$, two tailed.

An analysis of variance (ANOVA) model was generated to compare body fat mass responses (changes) between groups. If necessary, transformations were applied prior to running ANOVA in order to improve kurtosis and/or skew. Changes within treatment groups were evaluated by a one-sample t-test. All other outcome measurements were also analyzed using ANOVA models.

Results

Body Composition

Figure 2:
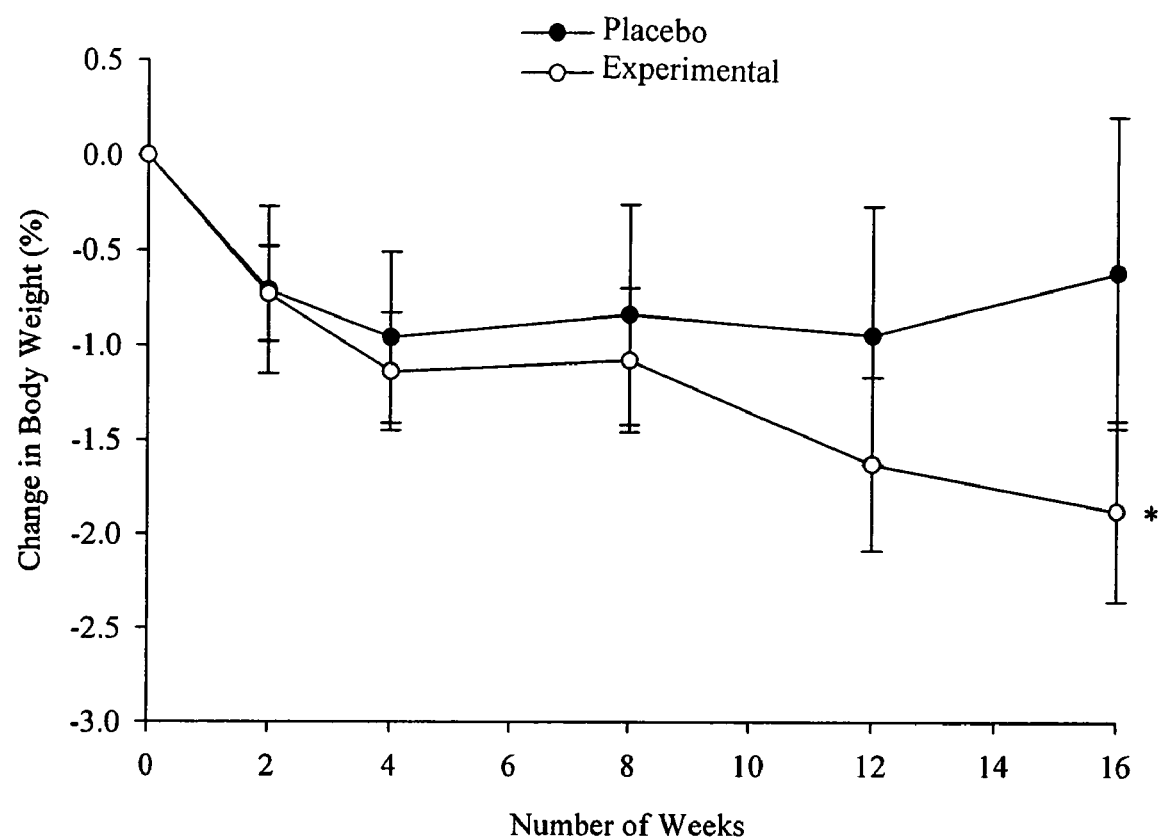
FIG. 2 is a graph illustrating the change in total body weight with a composition in accordance with the present invention as compared with a placebo.

FIG. 1 shows the percent change from baseline in the body fat mass (FM) of the per protocol sample. Both groups showed a significant decrease in FM during the treatment period. The experimental group lost significantly more than the control group (−5.8% vs. −2.3%, respectively, p=0.0425). FIG. 2 shows the percent change from baseline in body weight. Although the control group lost body weight (−0.6%), mean body weight did not decrease beyond week 4. In the experimental group, body weight continued to decline beyond week 4, showing a maximum reduction of 1.8% at week 16 (p=0.0014).

Table 7 shows additional values for anthropometric measures and body composition. Within group changes in body weight and FM were significant for the experimental group (p≦0.002 for both), while only the change in FM reached significance for the control group (p=0.0240). Lean body mass and waist circumference did not differ between or within groups at baseline or at week 16. Although weight loss is typically accompanied by loss of lean tissue as well as fat tissue, there generally was no loss of lean body mass in this experiment.

TABLE 7

| Parameter | Control[1] (n = −23) | Experimental[1] (n = 18) | p-values |
|---|---|---|---|
| Fat Mass[2] (kg) | | | |
| Week 1 | 35.5 ± 1.7 | 33.0 ± 1.5 | 0.3081 |
| Week 16 | 34.6 ± 1.7 | 31.4 ± 1.7 | 0.1857 |
| Δ from Week 0 to 15 | −0.9 ± 0.4* | −1.7 ± 0.3‡ | 0.0980 |
| Body Weight (kg) | | | |
| Week 0 | 94.0 ± 0.4 | 91.7 ± 2.6 | 0.6060 |
| Week 16 | 93.3 ± 3.3 | 89.9 ± 2.5 | 0.4398 |
| Δ from Week 0 to 16 | −0.7 ± 0.7 | −1.8 ± 0.5‡ | 0.2597 |
| Lean Mass[2] (kg) | | | |
| Week 0 | 50.5 ± 1.9 | 51.5 ± 2.3 | 0.7541 |
| Week 16 | 51.0 ± 1.9 | 51.9 ± 2.2 | .07791 |
| Δ from Week 0 to 16 | 0.5 ± 0.3 | 0.4 ± 0.3 | 0.8092 |

[1]Values are mean +/− standard error of the mean for all parameters.
[2]All values for fat mass and lean mass determined via DEXA (dual energy x-ray absorptiometry).
Within group changes are marked as follows:
*p < 0.05;
†p < 0.01;
‡p < 0.001.

Because there were significant differences in some dietary parameters at baseline, the least squares mean changes are reported in Table 7 based on models containing the baseline value as a covariate. The total energy intake did not change significantly within the two groups, despite a targeted reduction of between about 500-800 calories per day. In the experimental group, total energy intake was reduced by 20 calories per day. In comparison, in the control group, total energy intake was reduced by 264 calories per day. Calcium increased significantly in the experimental group (p<0.0001 both within and between groups), due to the added calcium in the study product. In addition, percent energy from protein was significantly different at end-of-treatment between groups (p=0.0036). These two changes are consistent with the nutrient composition of the study product.

While particular embodiments of the present invention have been described and illustrated, it should be understood that the invention is not limited thereto since modifications may be made by persons skilled in the art. The present application contemplates any and all modifications that fall within the spirit and scope of the underlying invention disclosed and claimed herein.

What is claimed is:

1. A method for decreasing fat mass and body weight in a human subject consuming a hypocaloric diet, the method comprising administering to the subject a composition comprising from about 2 to about 20 grams per serving of angiotensin converting enzyme-inhibiting peptides, from about 3 to about 10 grams per serving of κ-casein fragment 106-109, and from about 0.5 to about 6 grams per serving of calcium, the angiotensin converting enzyme-inhibiting peptides, κ-casein fragment 106-109, and calcium being derived from milk.

2. The method of claim 1 wherein the composition comprises from about 4 to about 20 grams per serving of angiotensin converting enzyme-inhibiting peptides, from about 4 to about 10 grams per serving of κ-casein fragment 106-109, and from about 1 to about 6 grams per serving of calcium, the angiotensin-converting enzyme-inhibiting peptides, κ-casein fragment 106-109, and calcium being derived from milk.

3. The method of claim 1 wherein the hypocaloric diet is a mildly hypocaloric diet.

4. The method of claim 1 wherein the hypocaloric diet reduces energy intake by at least 20 calories per day.

* * * * *